(12) United States Patent
Olson

(10) Patent No.: US 7,297,835 B2
(45) Date of Patent: Nov. 20, 2007

(54) ABSORBENT ARTICLE FEATURING A TEMPERATURE CHANGE MEMBER

(75) Inventor: Christopher P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/245,870

(22) Filed: Oct. 7, 2005

(65) Prior Publication Data

US 2007/0083172 A1    Apr. 12, 2007

(51) Int. Cl.
*A61F 13/15* (2006.01)

(52) U.S. Cl. .................. 604/364; 604/361; 604/367

(58) Field of Classification Search .............. 604/361, 604/364, 367, 380, 96, 108, 114
See application file for complete search history.

(56) References Cited

U.S. PATENT DOCUMENTS

| | | | |
|---|---|---|---|
| 3,375,827 A * | 4/1968 | Bletzinger et al. .......... 604/380 |
| 3,849,241 A | 11/1974 | Butin et al. | |
| 4,100,324 A | 7/1978 | Anderson et al. | |
| 4,375,448 A | 3/1983 | Appel et al. | |
| 4,507,121 A * | 3/1985 | Leung .................. 604/361 |
| 4,604,313 A | 8/1986 | Mcfarland et al. | |
| 4,663,220 A | 5/1987 | Wisneski et al. | |
| 4,704,116 A | 11/1987 | Enloe | |
| 4,940,464 A | 7/1990 | Van Gompel et al. | |
| 5,046,272 A | 9/1991 | Vogt et al. | |
| 5,104,116 A | 4/1992 | Pohjola | |
| 5,114,781 A | 5/1992 | Morman | |
| 5,116,662 A | 5/1992 | Morman | |
| 5,156,902 A | 10/1992 | Pieper et al. | |
| 5,163,425 A * | 11/1992 | Nambu et al. .............. 607/110 |
| 5,224,405 A | 7/1993 | Pohjola | |
| 5,226,992 A | 7/1993 | Morman | |
| 5,266,592 A | 11/1993 | Grub et al. | |
| 5,284,703 A | 2/1994 | Everhart et al. | |
| 5,348,750 A | 9/1994 | Greenberg | |
| 5,350,624 A | 9/1994 | Georger et al. | |
| 5,486,166 A | 1/1996 | Bishop et al. | |
| 5,490,846 A | 2/1996 | Ellis et al. | |
| 5,575,785 A | 11/1996 | Gryskiewicz et al. | |
| 5,645,542 A | 7/1997 | Anjur et al. | |
| 5,681,298 A | 10/1997 | Brunner et al. | |
| 5,766,389 A | 6/1998 | Brandon et al. | |
| 5,769,835 A | 6/1998 | Fell et al. | |
| 5,883,028 A | 3/1999 | Morman et al. | |
| 5,935,118 A | 8/1999 | Gryskiewicz et al. | |
| 5,964,743 A | 10/1999 | Abuto et al. | |
| 6,126,648 A | 10/2000 | Keck et al. | |
| 6,231,557 B1 | 5/2001 | Krautkramer et al. | |
| 6,362,389 B1 | 3/2002 | Mcdowall et al. | |
| 6,552,245 B1 | 4/2003 | Roessler et al. | |

(Continued)

FOREIGN PATENT DOCUMENTS

EP    0 217 032 A2    4/1987

(Continued)

*Primary Examiner*—Jacqueline F. Stephens
(74) *Attorney, Agent, or Firm*—Randall W. Fieldhack (57) ABSTRACT

Disclosed is an absorbent article including a temperature change member. The temperature change member includes temperature change material disposed with the temperature change member in a nonuniform distribution by weight across the temperature change member.

24 Claims, 7 Drawing Sheets

U.S. PATENT DOCUMENTS

| | | |
|---|---|---|
| 6,627,786 B2 | 9/2003 | Roe et al. |
| 6,642,427 B2 | 11/2003 | Roe et al. |
| 6,645,190 B1 | 11/2003 | Olson et al. |
| 2003/0125682 A1 | 7/2003 | Olson et al. |
| 2004/0030310 A1 | 2/2004 | Roe et al. |
| 2004/0254549 A1 | 12/2004 | Olson et al. |
| 2006/0069363 A1 | 3/2006 | Weber et al. |
| 2006/0142714 A1 | 6/2006 | Jackson et al. |

FOREIGN PATENT DOCUMENTS

| | | |
|---|---|---|
| WO | WO 9619168 A2 * | 6/1996 |
| WO | WO 9619172 A1 * | 6/1996 |
| WO | WO 00/37009 A2 | 6/2000 |
| WO | WO 01/88245 A2 | 11/2001 |
| WO | WO 2003/051254 A2 | 6/2003 |
| WO | WO 2006/071526 A1 | 7/2006 |

\* cited by examiner

ABSORBENT ARTICLE FEATURING A TEMPERATURE CHANGE MEMBER

BACKGROUND OF THE INVENTION

The present invention relates to absorbent articles that include a temperature change member. More specifically, the invention relates to an absorbent article such as training pants that provides the wearer with a noticeable temperature change sensation upon urination.

Absorbent articles such as disposable diapers and training pants are useful to absorb and contain body wastes. These products have developed to the extent that urine is quickly drawn and retained away from the wearer's skin so that the wearer remains relatively dry and comfortable. Although this improved performance enhances wearer dryness and comfort, it can reduce the wearer's ability to notice or recognize when urination occurs, especially if the wearer's attention is distracted by an activity. This is not conducive to toilet training because an important step in the early stages of toilet training is the ability to recognize when urination occurs. In an attempt to enhance a child's recognition of when urination occurs, training pants have been designed with temperature change members that provide a temperature change sensation upon urination.

Unfortunately, in certain circumstances, such temperature change members may not be completely satisfactory. For example, articles can, in certain circumstances, deform during use, particularly between the wearer's legs. As such, an article including a temperature change member may shift position and be less effective at alerting a wearer of urination if it is also spaced from the skin of the wearer.

Thus, there is a need for an absorbent article with a temperature change member that is more capable of effectively alerting the wearer in use, particularly in conditions where the temperature chamber could typically shift position. Further, there is a need for an absorbent article that is more likely to alert a wearer to urination even after the article has been deformed between the wearer's legs in use.

SUMMARY OF THE INVENTION

In one aspect, the present invention is directed to an absorbent article defining a longitudinal direction, a lateral direction perpendicular to the longitudinal direction, an article first side edge and an article second side edge opposite the article first side edge and a pair of end edges. The absorbent article includes a liquid impermeable outercover, an absorbent body disposed on the outercover, and a temperature change member disposed with the absorbent body. The temperature change member includes temperature change material disposed with the temperature change member in a nonuniform distribution by weight across the temperature change member in the lateral direction. The temperature change member also provides the article with a temperature change of at least 5 degrees C., as determined by the temperature change test described herein.

In another aspect, the present invention is directed to an absorbent article defining a longitudinal direction, a lateral direction perpendicular to the longitudinal direction, an article first side edge and an article second side edge opposite the article first side edge and a pair of end edges. The absorbent article includes a liquid impermeable outercover, an absorbent body disposed on the outercover, and a temperature change member disposed with the absorbent body. The temperature change member defines a temperature change member first side edge, a temperature change member second side edge opposite the temperature change member first side edge, a first temperature change member region, a second temperature change member region, and a third temperature change member region between the first temperature change member region and the second temperature change member region. The temperature change member includes temperature change material disposed with the temperature change member in a nonuniform distribution by weight across the temperature change member in the lateral direction. The first temperature change member region and the second temperature change member region include a greater amount of temperature change material by weight than the third temperature change member region. The temperature change member provides the article with a temperature change of at least 5 degrees C., as determined by the temperature change test described herein.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

DEFINITIONS

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 50 percent (to 150 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Join" and its derivatives refer to the connecting, adhering, bonding, attaching, sewing together, or the like, of two elements. Two elements will be considered to be joined together when they are integral with or joined directly to one another or indirectly to one another, such as when each is directly joined to intermediate elements. "Join" and its derivatives include permanent, releasable, or refastenable joinder. In addition, the joining can be completed either during the manufacturing process or by the end user.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Such a process is disclosed, for example, in U.S. Pat. No. 3,849,241 to Butin et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Stretchable" means that a material can be stretched, without breaking, by at least 50 percent (to 150 percent of its initial (unstretched) length) in at least one direction. Elastic materials and extensible materials are each stretchable materials.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Figure 1:
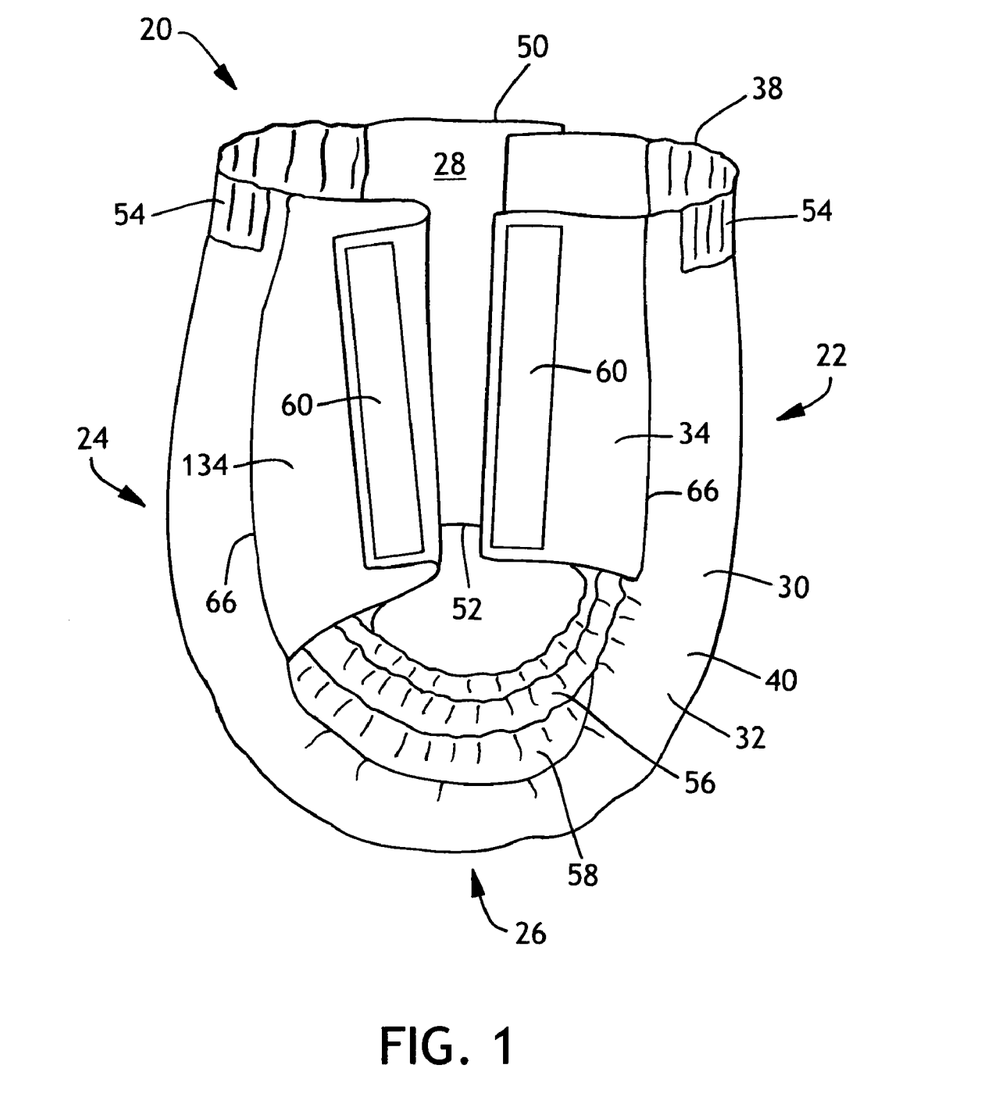
FIG. 1 representatively illustrates a side view of a pair of training pants with a mechanical fastening system of the pants shown fastened on one side of the training pants and unfastened on the other side of the training pants.

Referring now to the drawings and in particular to FIG. 1, an absorbent article of the present invention is representatively illustrated in the form of children's toilet training pants and is indicated in its entirety by the reference numeral 20. The pants 20 include a temperature change member 70 that is adapted to create a distinct temperature change sensation to the wearer upon urination, which can enhance a wearer's ability to recognize when urination is occurring.

The pants 20 may or may not be disposable, which refers to articles that are intended to be discarded after a limited period of use instead of being laundered or otherwise conditioned for reuse. It should also be understood that the present invention can be suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson, et al. which are incorporated herein by reference to the extent that they are consistent (i.e., not in conflict) herewith. In addition, absorbent articles including a temperature change member are described in U.S. Pat. No. 5,681,298 to Brunner et al., and U.S. patent application Ser. No. 11/143,359 filed Jun. 1, 2005 in the name of Jackson, et al., the disclosures of which are incorporated herein by reference to the extent that they are consistent (i.e., not in conflict) herewith.

Figure 2:
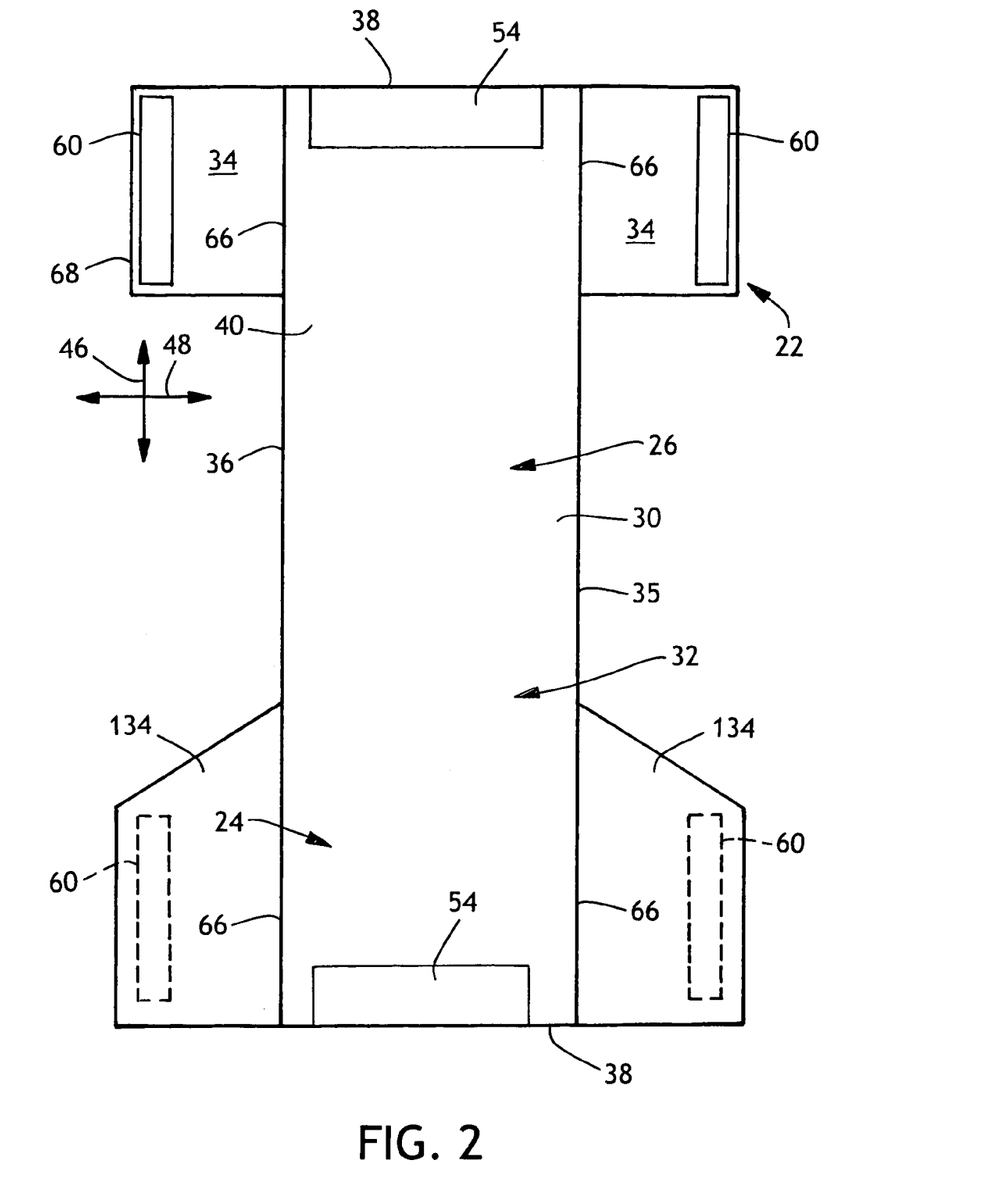
FIG. 2 representatively illustrates a plan view of the training pants of FIG. 1 in an unfastened, stretched and laid flat condition, and showing the surface of the training pants that faces away from the wearer.
Figure 3:
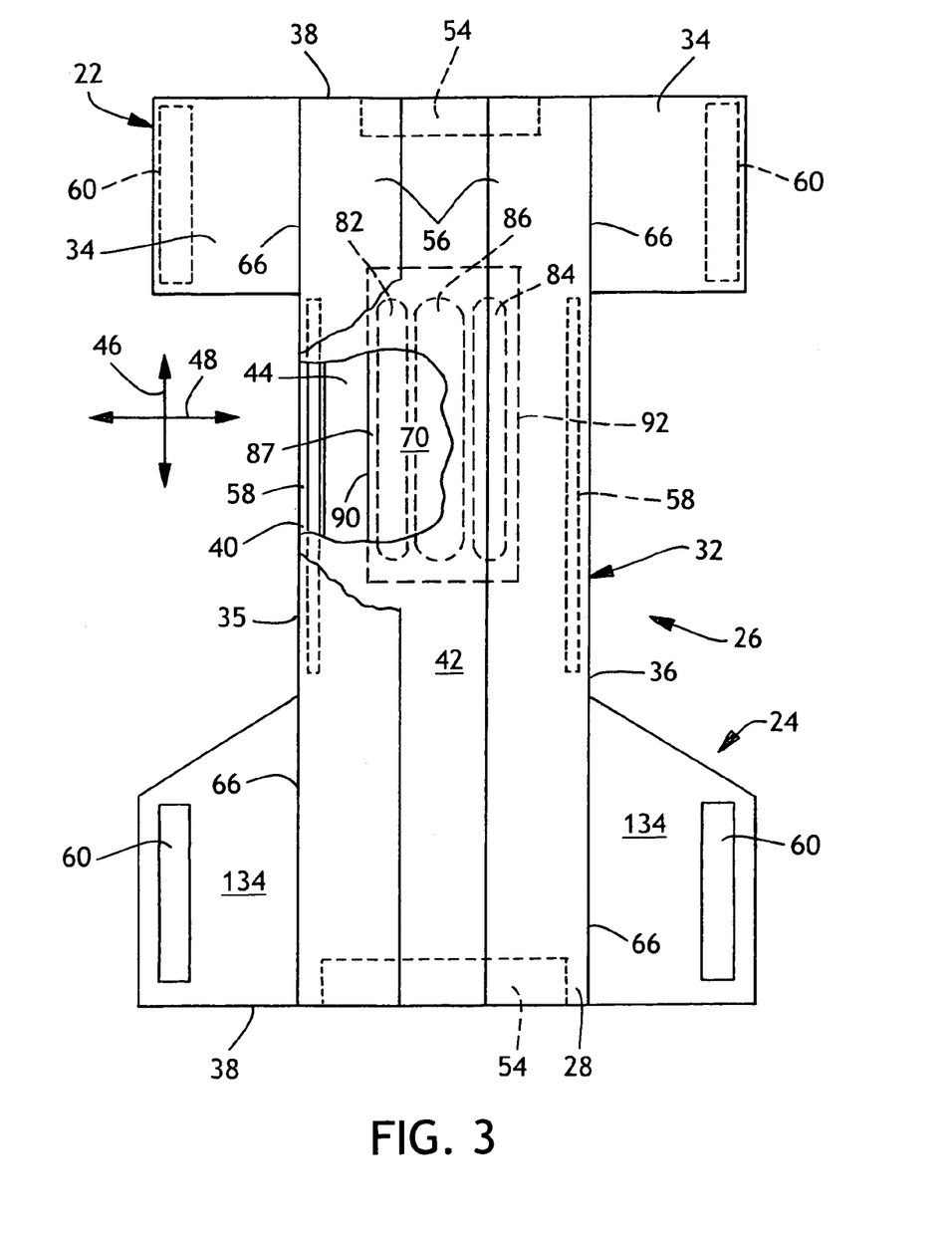
FIG. 3 representatively illustrates a plan view similar to FIG. 2, but showing the surface of the training pants that faces the wearer when worn, and with portions cut away to show underlying features.

The training pants 20 are illustrated in FIG. 1 in a partially fastened condition. The pants 20 define a longitudinal direction 46 and a lateral direction 48 perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 includes those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use to be disposed toward the wearer, and an outer surface 30 opposite the inner surface. With additional reference to FIGS. 2 and 3, the pair of training pants 20 has a longitudinally extending first side edge 35 and a longitudinally extending second side edge 36 opposite the first side edge, and a pair of laterally extending opposing waist edges 38 (broadly, end edges).

The illustrated pants 20 can include an absorbent assembly, generally indicated at 32. For example, in the aspect of FIGS. 1-3, the training pants 20 include a generally rectangular central absorbent assembly 32 and side panels 34, 134 formed separately from and secured to the central absorbent assembly. The side panels 34, 134 can be bonded along seams 66 to the absorbent assembly 32 in the respective front and back waist regions 22 and 24 of the pants 20. More particularly, the front side panels 34 can be permanently bonded to and extend laterally outward from the absorbent assembly 32 at the front waist region 22, and the back side panels 134 can be permanently bonded to and extend laterally from the absorbent assembly 32 at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus include the portions of the training pants 20 that are positioned on the hips of the wearer. The front and back side panels 34 and 134 can be permanently bonded together to form the three-dimensional configuration of the pants 20, or be releasably connected with one another such as by a fastening system 60 of the illustrated aspects.

Suitable elastic materials, as well as processes for incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference in their entirety to the extent they are consistent (i.e., not in conflict) herewith. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the side panels 34, 134 may include elastic material or stretchable but inelastic materials.

The absorbent assembly 32 is illustrated in FIGS. 2-3 as having a rectangular shape. However, it is contemplated that the absorbent assembly 32 may have other shapes (e.g., hourglass, T-shaped, I-shaped, and the like) without departing from the scope of this invention. It is also understood that the side panels 34,134 may alternatively be formed integrally with the absorbent assembly 32 without departing from the scope of this invention. In such a configuration, the side panels 34 and 134 and the absorbent assembly would include at least some common materials, such as the bodyside liner 42, outercover 40, other materials and/or combinations thereof.

Figure 7:
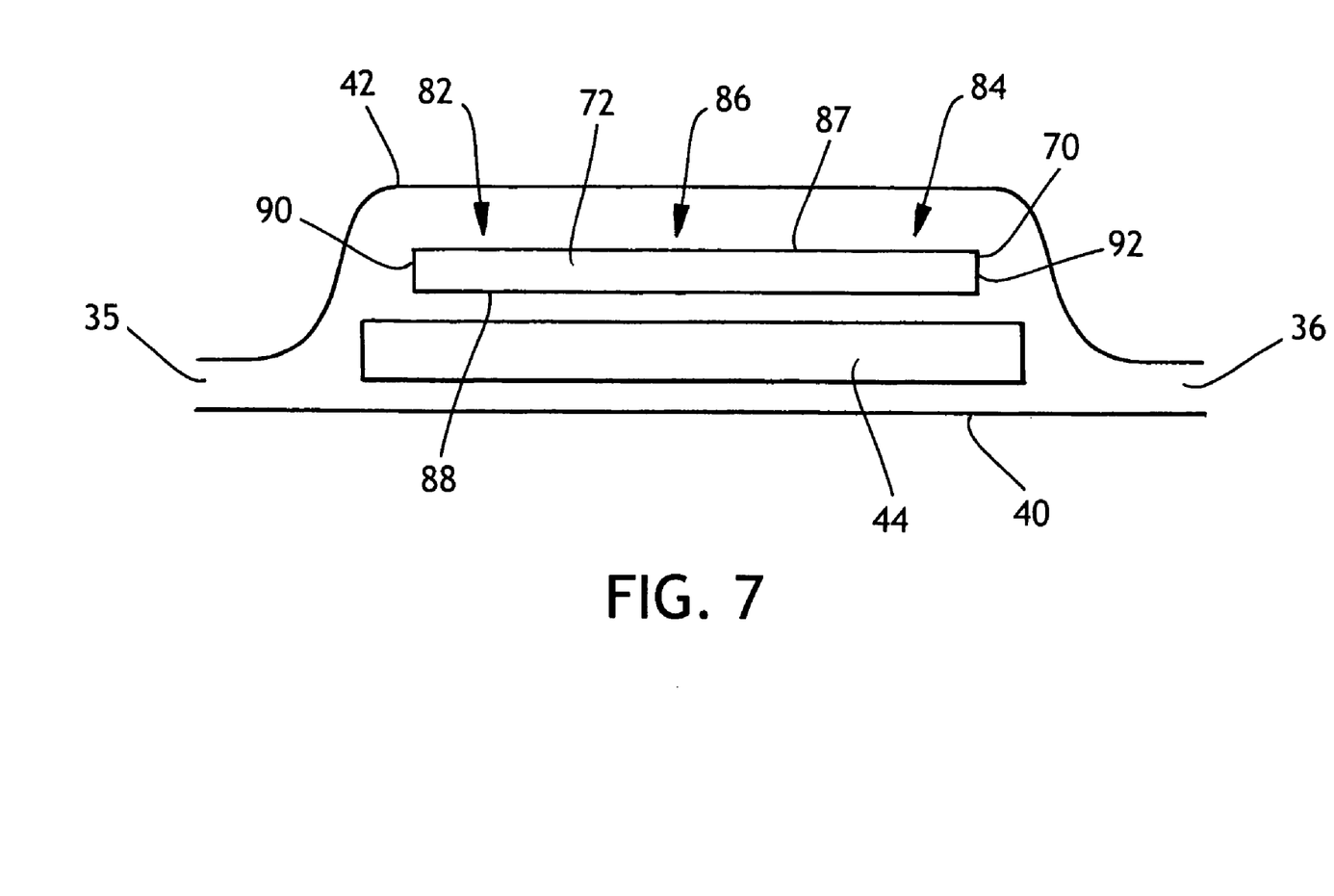
FIG. 7 representatively illustrates a section view of another aspect of the training pants with elements removed for clarity.

The absorbent assembly 32 includes an outercover 40 and a bodyside liner 42 (FIGS. 3, 7) in a superposed relation therewith. The liner 42 can be suitably joined to the outercover 40 along at least a portion of the longitudinal ends of the pants 20. The liner 42 can be suitably adapted, i.e., positioned relative to the other components of the pants 20, to contact the wearer's skin during wear of the pants. The absorbent assembly 32 also includes an absorbent body 44 (FIGS. 3, 7) disposed between the outercover 40 and the bodyside liner 42 for absorbing liquid body exudates. The liner 42 can be suitably joined to the outercover 40 along at least a portion of the absorbent assembly 32. The bodyside liner 42 and the outercover 40 can, for example, be attached to each other by adhesive, ultrasonic bonding, thermal bonding or by other suitable attachment techniques known in the art. Moreover, at least a portion of the absorbent body 44 can optionally be attached to the bodyside liner 42 and/or the outercover 40 utilizing the methods described above.

As mentioned above, the front and back side panels 34 and 134 can be releasably connected with one another such as by the fastening system 60 of the illustrated aspect. With the training pants 20 in the fastened position as partially illustrated in FIG. 1, the front and back waist regions are connected together to define the three-dimensional pants configuration having a waist opening 50 and a pair of leg openings 52. The waist edges 38 (e.g., longitudinal ends) of the training pants 20 are configured to encircle the waist of the wearer to define the waist opening 50 (FIG. 1) of the pants.

The fastening system 60 may include any refastenable fasteners suitable for absorbent articles, such as adhesive fasteners, cohesive fasteners, mechanical fasteners, or the like. In one aspect of the invention, the fastening system includes mechanical fastening elements for improved performance. Suitable mechanical fastening elements can be provided by interlocking geometric-shaped materials, such as hooks, loops, bulbs, mushrooms, arrowheads, balls on stems, male and female mating components, buckles, snaps, or the like. For example, fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The pants 20 may further include a pair of containment flaps 56 for inhibiting the lateral flow of body exudates. As illustrated in FIG. 3, the containment flaps 56 can be operatively attached to the pants 20 in any suitable manner as is well known in the art. In particular, suitable constructions and arrangements for the containment flaps 56 are generally well known to those skilled in the art and are described in U.S. Pat. No. 4,704,116 issued Nov. 3, 1987 to Enloe, which is incorporated herein by reference to the extent that it is consistent (i.e., not in conflict) herewith.

To further enhance containment and/or absorption of body exudates, the training pants 20 may include waist elastic members 54 in the front and/or back waist regions 22 and 24 of the pants 20. Likewise, the pants 20 may include leg elastic members 58, as are known to those skilled in the art. The waist elastic members 54 and the leg elastic members 58 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament elastomeric threads sold under the trade name LYCRA and available from Invista of Wilmington, Del., U.S.A.

The outercover 40 may suitably include a material that is substantially liquid impermeable. The outercover 40 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outercover 40 may include a woven or non-woven fibrous web layer that has been totally or partially constructed or treated to impart the desired levels of liquid impermeability to selected regions that are adjacent or proximate the absorbent body.

The outercover 40 may also be stretchable, and in some aspects it may be elastomeric. For example, such an outercover material can include a 0.3 osy polypropylene spunbond that is necked 60 percent in the lateral direction 40 and creped 60 percent in the longitudinal direction 48, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outercover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent body 44. A suitable liquid permeable bodyside liner 42 is a nonwoven polyethylene/polypropylene bicomponent web having a basis weight of about 27 gsm; the web may be spunbonded or a bonded carded web. Optionally, the bodyside liner 42 may be treated with a surfactant to increase the wettability of the liner material.

Alternatively, the bodyside liner 42 may also be stretchable, and in some aspects it may be elastomeric. For instance, the liner 42 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., which is incorporated by reference herein to the extent that it is consistent (i.e., not in conflict) herewith.

An absorbent body 44 may be disposed on the outercover 40, for example, between the outercover 40 and the bodyside liner 42. The outercover 40 and the bodyside liner 42 can be joined together by any suitable means such as adhesives, ultrasonic bonds, thermal bonds, or the like. The absorbent body 44 can be in a variety of shapes and configurations as are known in the art, such as rectangular, hourglass shaped, I-shaped, and the like. Further, at least a portion of the absorbent body 44 can optionally be attached to the bodyside liner 42 and/or the outercover 40 utilizing the methods described above.

The absorbent body 44 is suitably compressible, conformable and capable of absorbing and retaining liquid body exudates released by the wearer. For example, the absorbent assembly can include a matrix of absorbent fibers, and more suitably cellulosic fluff, such as wood pulp fluff, and superabsorbent particles. One suitable pulp fluff is identified with the trade designation CR1654, commercially available from Bowater, Inc. of Greenville, S.C., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

In one aspect, the absorbent body 44 may be stretchable so as not to inhibit the stretchability of other components to which the absorbent body may be adhered, such as the outercover 40 and/or the bodyside liner 42. For example, the absorbent body may include materials disclosed in U.S. Pat. Nos. 5,964,743, 5,645,542, 6,231,557, 6,362,389, and international patent application WO 03/051254, the disclosure of each of which is incorporated by reference herein.

In some aspects, a surge management layer (not shown) may be included in the pants 20. The surge management layer may be positioned in the pants 20 in a variety of locations as is known in the art. For example, the surge management layer can be proximate the absorbent body 44, for example between the absorbent body 44 and the bodyside liner 42, and attached to one or more components of the pants 20 by methods known in the art, such as by adhesive, ultrasonic or thermal bonding. In addition, the surge management layer may be positioned in the pants 20 relative to the temperature change member 70 in a variety of ways. For instance, the surge management layer may be disposed toward the liner 42 relative to the temperature change member 70, or the surge management layer may be disposed toward the absorbent body 44 relative to the temperature change member 70.

A surge management layer helps to decelerate and diffuse surges or gushes of liquid that may be rapidly introduced into the absorbent body 44. Desirably, the surge management layer can rapidly accept and temporarily hold the liquid prior to releasing the liquid into the storage or retention portions of the absorbent body 44. Examples of suitable surge management layers are described in U.S. Pat. No. 5,486,166 and U.S. Pat. No. 5,490,846, the contents of which are incorporated herein by reference to the extent that they are consistent (i.e., not in conflict) herewith.

As mentioned above, the various aspects of the absorbent article of the present invention can also include a temperature change member 70 (FIGS. 3-7). The temperature change member 70 can include a temperature change member first surface and a temperature change member second surface opposite the first surface. For example, as representatively illustrated in FIGS. 4-8, the temperature change member 70 can include a temperature change member bodyfacing surface 87 and a temperature change member garment facing surface 88 opposite the bodyfacing surface 87. The temperature change member 70 can also define a pair of longitudinally extending side edges, such as a temperature change member first side edge 90 and a temperature change member second side edge 92 opposite the temperature change member first side edge 90.

Figure 4:
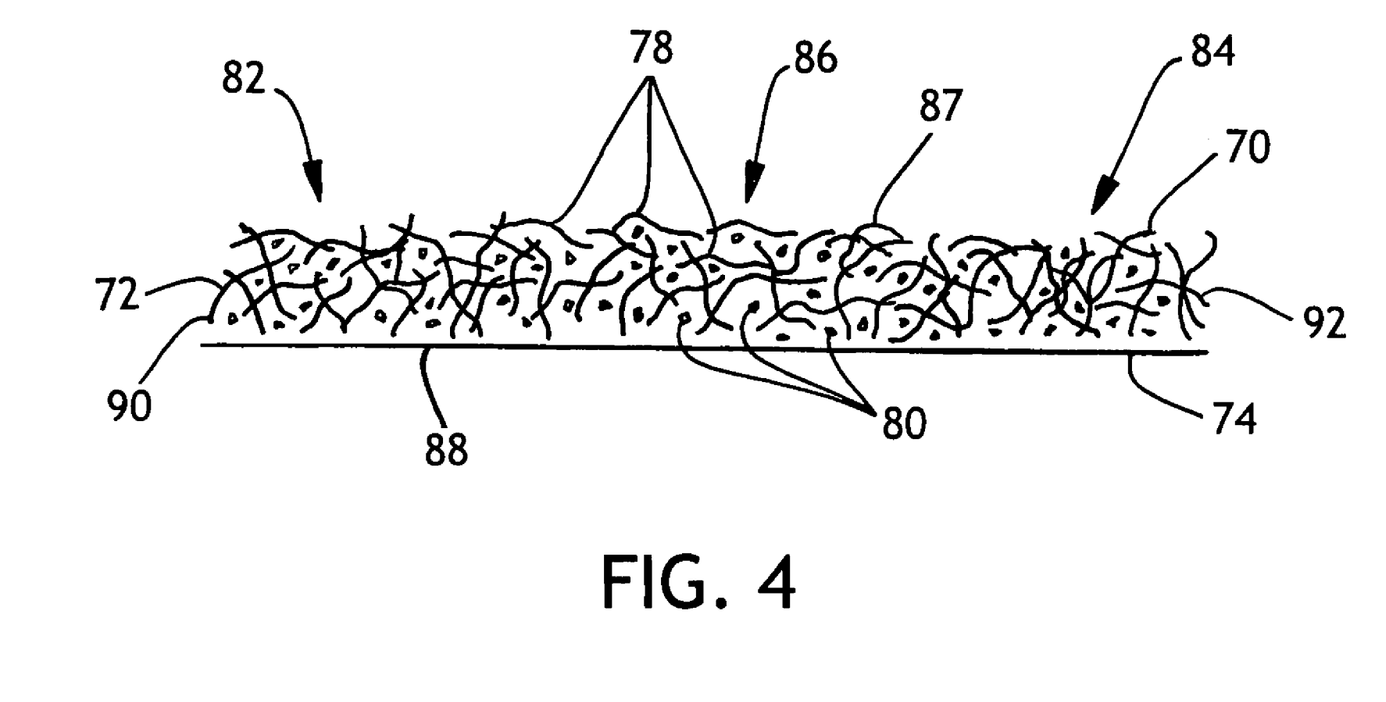
FIG. 4 representatively illustrates a section view of a particular aspect of the temperature change member of the present invention.
Figure 5:
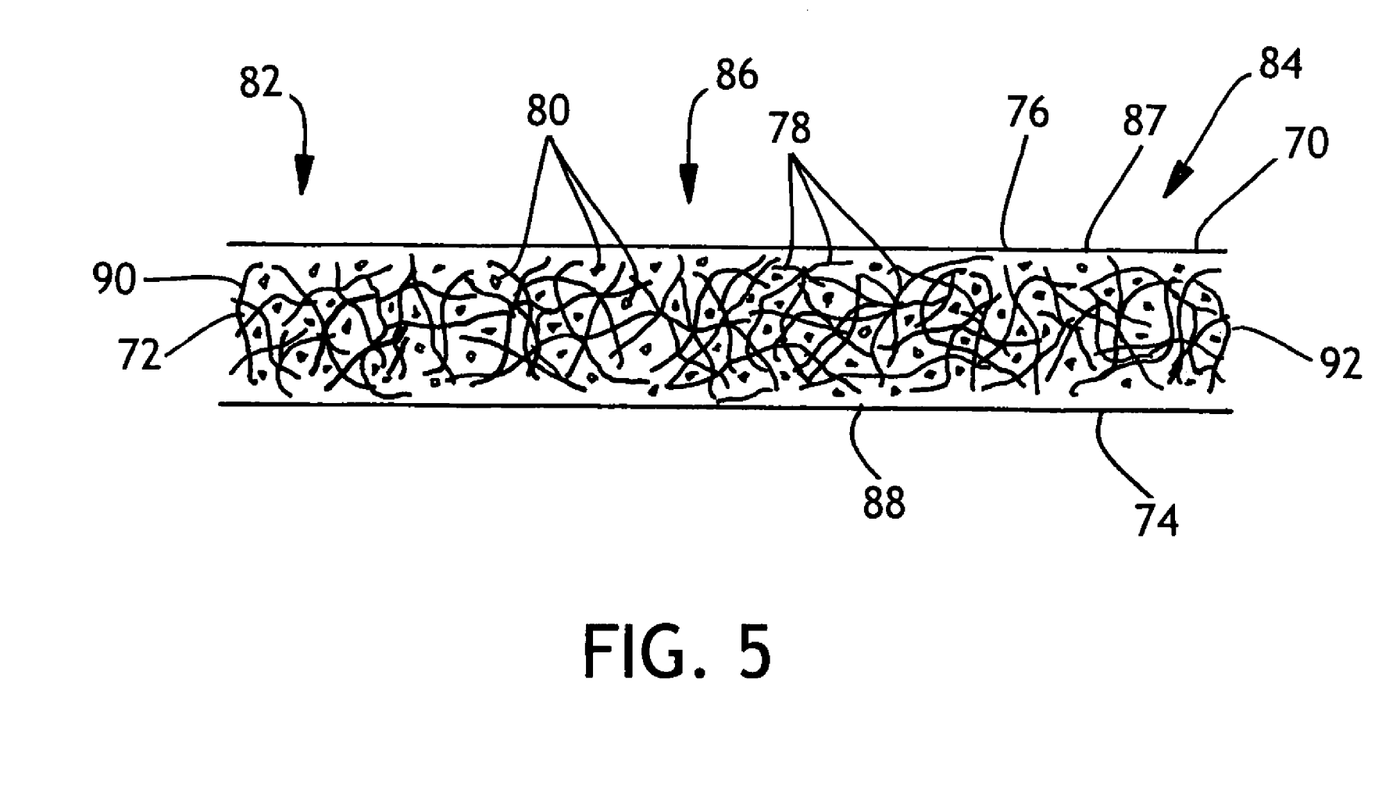
FIG. 5 representatively illustrates a section view of another aspect of the temperature change member of the present invention.
Figure 6:
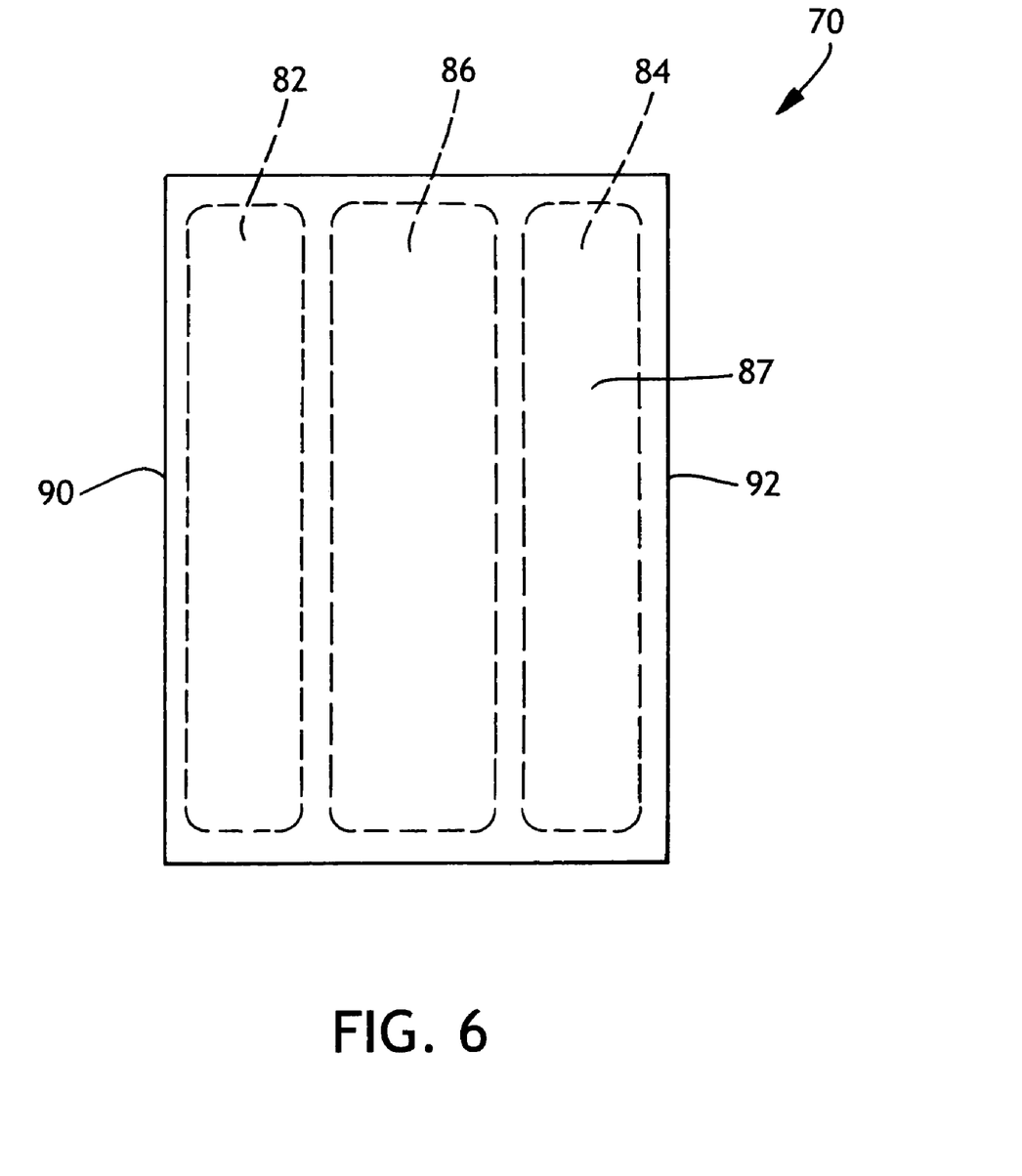
FIG. 6 representatively illustrates a plan view of an example of a temperature change member of the present invention.

The temperature change member 70 can include temperature change material 80 (FIGS. 4-5). The temperature change material 80 can be disposed with the temperature change member 70 in a variety of configurations. For example, the temperature change material 80 can be distributed in a substantially uniform manner throughout the temperature change member 70, such that all areas or regions of the temperature change member have substantially equal amounts of temperature change material, measured by weight. Alternatively, the temperature change material 80 can be suitably disposed with the temperature change member 70 in a nonuniform distribution, measured by weight. In such an aspect, the temperature change material can be strategically located to maximize the effectiveness of the temperature change member 70 in use and to better manage the raw material costs of the temperature change material 80.

Thus, in one aspect, the temperature change material 80 can be disposed with the temperature change member 70 in a nonuniform distribution by weight across the temperature change member in the lateral direction 48. In such an arrangement, temperature change material 80 can be disposed with the temperature change member 70 in greater or lesser amounts (measured by weight) in some regions of the temperature change member 70 than in other regions of the temperature change member 70. In particular, in at least one cross section of the temperature change member 70 having some lateral direction 48 component (i.e., the cross section is not taken exclusively in the longitudinal direction 46), the distribution of temperature change material 80 can be suitably nonuniform across the cross section. Nonetheless, despite this nonuniformity of temperature change material 80 in the temperature change member 70 in the lateral direction 48, the temperature change material 80 can optionally be substantially uniformly distributed in the temperature change member in the longitudinal direction 46 for improved manufacturability.

For example, the temperature change member 70 can define a plurality of temperature change member regions. For example, as representatively illustrated in FIGS. 3-7, the temperature change member 70 can define a first temperature change member region 82, and a second temperature change member region 84. The temperature change member 70 can also optionally define a third temperature change member region 84 between the first temperature change member region 82 and the second temperature change member region 86. As representatively illustrated in FIGS. 3-7, the temperature change member regions 82, 84, and 86 can be distributed across the temperature change member 70 generally in the lateral direction 48. That is, the distribution of the regions 82, 84, and 86 includes a component in the lateral direction 48 and is not completely perpendicular to the lateral direction 48. In a particular aspect, the first temperature change member region 82 can be proximate the temperature change member first side edge 90 and the second temperature change member region 84 can be proximate the temperature change member second side edge 92, with the third temperature change member region 86 disposed between the first and second temperature change member regions 82 and 84 (FIGS. 3-7).

Suitably, each of the temperature change member regions 82, 84, and 86 can be at least 10% of the total area of the temperature change member 70, and more suitably at least 20% of the total area of the temperature change member 70. Moreover, as can be readily appreciated, the temperature change member regions 82, 84, and 86 can be a variety of shapes and sizes. For example, the temperature change member regions 82, 84, and 86 can be generally rectangular (FIGS. 3 and 6), circular, oval, triangular and the like or combinations thereof. In addition, the temperature change members 82, 84, and 86 may be generally the same shape or they may have different shapes.

Accordingly, the temperature change material 80 can be distributed in the temperature change member regions 82, 84 and 86 in nonuniform amounts, by weight. For example, the first temperature change member region 82 can include a greater amount of temperature change material 80 than the third temperature change member region 86. Likewise, the second temperature change member region 84 can include a greater amount of temperature change material 80 than the third temperature change member region 86. Alternatively, the third temperature change member region 86 can include a greater amount of temperature change material 80 than one or both of the first and second temperature change member regions 82 and 84. Likewise, the first temperature change member region 82 can include a greater or lesser amount of temperature change material 80 than the second temperature change member region 84.

Nonetheless, In the above aspects, a selection of the temperature change member regions 82, 84, and 86 can optionally include substantially the same amount of temperature change material 80 (by weight) while maintaining a nonuniform distribution of temperature change material 80 across the temperature change member 70 in the lateral direction 48. For example, the first and second temperature change member regions 82 and 84 can include substantially the same amount of temperature change material 80 while the third temperature change member region 86 includes a greater or lesser amount of temperature change material 80. Similarly, the first and third temperature change member regions 82 and 86 can include substantially the same amount of temperature change material 80 while the second temperature change member region 84 includes a greater or lesser amount of temperature change material 80. In addition, the second and third temperature change member regions 84 and 86 can include substantially the same amount of temperature change material 80 while the first temperature change member region 86 includes a greater or lesser amount of temperature change material 80.

As can be appreciated, the temperature change member 70 can define a total amount of temperature change material 80, by weight. For example, in one aspect, the temperature change member 70 can include 1 to 30 grams of material 80, and in particular, 1 to 20 grams of material 80. In yet another alternative, the temperature change member 70 can include 1 to 10 grams of material 80.

Thus, in particular aspects, the third temperature change member region 86 can contain at least 10%, and optionally at least 15%, of the total amount of temperature change material 80 included in the temperature change member 70, by weight. Alternatively, the third temperature change member region 86 can contain less than 5%, and optionally 0%, of the total amount of temperature change material 80 included in the temperature change member 70, by weight. In these aspects, one of the first and second temperature change member regions 82 and 84, or each of the first and second temperature change member regions 82 and 84, can optionally include at least 10% more temperature change material 80 than the third temperature change member region 86, by weight. Further, the first and second temperature change member regions 82 and 84 together can comprise at least 60%, and optionally at least 85%, of the total amount of temperature change material 80 included in the temperature change member 70.

Nonuniform distribution of the temperature change material 80 in the temperature change member 70 can provide a number of benefits. For example, in situations where the temperature change member 70 is subject to deformation and shifting when the pants 20 are between the wearers legs in use, the temperature change material 80 can be concentrated in strategic locations within the temperature change member 70 to increase the effectiveness of the temperature change member under such conditions. Specifically, it was discovered that when the first and second temperature change member regions 82 and 84 were proximate the temperature change member side edges 90 and 92 they can have a greater likelihood of remaining in close body contact with the wearer when the pants 20 are squeezed between the legs of the wearer because of their proximity to the legs of the wearer. Further, if temperature change materials are strategically concentrated in certain locations of the temperature change member 70, a materials cost savings can be realized as a lesser amount of temperature change material 80 can optionally be utilized in other areas of the temperature change member 70.

The various regions 82, 84, and 86 of the temperature change member 70 can optionally be subjected to additional processing for improved performance. For example, the temperature change member 70 can be passed through a nip defined by opposed rolls in order to compress and densify all of the temperature change member 70 or certain regions 82, 84, and/or 86 of the temperature change member 70. Alternatively, other densification methods may be utilized as are well known to those skilled in the art. As such, the temperature change member 70 can define a density of between 0.20 grams per cm$^3$ to 0.55 grams per cm$^3$, particularly a density of between 0.25 grams per cm$^3$ to 0.45 grams per cm$^3$ and still more particularly, a density of 0.35 grams per cm$^3$ in at least the first temperature change member region 82 and the second temperature change member region 84, and optionally in the third temperature change member region 86. In another aspect, the third temperature change region 86 can remain uncompressed or define a lower density than the first and second temperature change member regions 82 and 84. Densities within these ranges are believed to allow provide a flexible yet robust temperature change member 70 that retains the temperature change material 80 within the matrix of fibers 78 and that has desirable integrity. Moreover, such densities are not so high as to crush or otherwise impair the temperature change material 80 thereby reducing its efficacy.

Increased densification in at least the first and second temperature change member regions 82 and 84 can make them more capable of resisting deformation and shifting when the pants 20 are between the wearer's legs in use. As such, at least the first and second temperature change member regions 82 and 84 of the temperature change member 70 have a greater likelihood of remaining in close body contact with the wearer when the pants 20 are squeezed between the legs of the wearer. That is, when the wearer squeezes the pants 20 between their legs, the temperature change member 70 may have a tendency to buckle with the rest of the crotch region 26 of the pants 20 and as a result, be forced away from the skin of the wearer. Nonetheless, with the temperature change member 70 of the present invention, at least the first and second temperature change member regions 82 and 84 can be configured to be more likely to resist buckling and remain in place (i.e., closer to the body of the wearer) and therefore be more effective in providing a temperature change to the wearer upon urination.

The temperature change member 70 can include a temperature change composite 72 and optionally a first carrier layer 74 in a superposed relationship with temperature change composite 72 (FIGS. 4 and 5). The temperature change member 70 can also optionally include a second carrier layer 76 where the first carrier layer 74 and the second carrier layer 76 sandwich the temperature change composite 72 (FIG. 5). As such, in aspects where the temperature change member 70 does not include carrier layers 74 or 76, the composite 72 can provide the surfaces 87 and 88 of the temperature change member 70. Alternatively, when present, the carrier layers 74 and 76 can provide one or both of the temperature change member surfaces 87 and 88.

The temperature change composite 72 includes temperature change material 80 and optionally, a matrix of fibers 78 where the temperature change material 80 is intermixed within the matrix of fibers 78. The matrix of fibers 78 may be substantially continuous or discrete and discontinuous. In addition, the matrix of fibers 78 of the temperature change composite 72 may be provided by a variety of different fibers as are known in the art. For example, the matrix of fibers 78 can include adhesive fibers, absorbent fibers, binders (including binder fibers), polymer fibers, and the like or combinations thereof. As such, the temperature change material 80 may be suitably entrapped within the matrix 78 to limit material shake-out or loss during manufacture and/or wear of the pants 20. Suitable temperature change composites 72 are described in U.S. Pat. No. 5,681,298 and U.S. patent application Ser. No. 11/143,359, each of which has been previously incorporated herein.

In particular, in aspects where the matrix of fibers 78 includes adhesive fibers, the fibers may be provided by a hot-melt adhesive. Such an adhesive generally comprises one or more polymers to provide cohesive strength, a resin or analogous material, perhaps waxes, plasticizers or other materials to modify viscosity, and/or other additives including, but not limited to, antioxidants or other stabilizers. It is also contemplated that alternative adhesives may be used without departing from the scope of this invention.

The temperature change material 80 can be intermixed with the adhesive fibers providing the matrix of fibers 78 by being fed into and entrained in a stream of adhesive to form a blended mixture of adhesive fibers and temperature change material 80. In such an aspect, the matrix of fibers can be optionally applied to a substrate, such as the first carrier layer 74. In addition, the second carrier layer 76 can, but need not, overlay the temperature change composite 72 and be secured thereto by the adhesive in the matrix of fibers 78.

An example of a suitable adhesive for use in providing the matrix of fibers 78 are hot-melt adhesives available from H. B. Fuller Adhesives of Saint Paul, Minn. under the designation HL8151-XZP. In particular, this adhesive is a hydrophilic adhesive which promotes the rapid wettability of the temperature change member 70 resulting in faster temperature change. Alternatively, it is contemplated that the adhesive can be a hydrophobic adhesive without departing from the scope of the present invention.

Alternatively, the matrix of fibers 78 of the temperature change composite 72 can include absorbent fibers. In such an aspect, the matrix of fibers 78 may be provided by absorbent fibers by forming the matrix on a forming surface of a conventional air-forming device. Suitable absorbent fibers can include natural absorbent fibers such as cellulosic fibers (i.e., wood pulp fibers) or cotton fibers, synthetic absorbent fibers such as rayon or cellulose acetate or combinations thereof. In particular, the absorbent fibers can be a mixed bleached southern softwood and hardwood Kraft pulp designated as CR1654 available from Bowater Inc. of Greenville, S.C. U.S.A. Other suitable absorbent fibers can include NB 416, a bleached southern softwood Kraft pulp available from Weyerhaeuser Co. of Federal Way, Wash. U.S.A.; CR 1654, a bleached southern softwood Kraft pulp available from Bowater, Incorporated, of Greenville, S.C. U.S.A.; SULPHATATE HJ, a chemically modified hardwood pulp available from Rayonier Inc. of Jesup, Ga. U.S.A. and NF 405, a chemically treated bleached southern softwood Kraft pulp available from Weyerhaeuser Co.

Optionally, in such an aspect, the matrix of fibers 78 can further include binder material. For example, the binder material can suitably be a thermoplastic binder material. Such binder materials can soften when exposed to heat and can substantially returns to their original condition when cooled to room temperature. Such thermoplastic binder materials, when in the softened state, constrain or entrap the fibers and other materials proximate the binder to stabilize the temperature change composite 72. Binder materials can be provided in powder or fiber form. Examples of suitable binder materials for use with the present invention can be those having low melting temperatures such as polyethylene glycol (PEG) or paraffin wax, both of which are available from Alrich of Saint Louis, Mo.

In yet another alternative the matrix of fibers 78 may be provided by a coform composite including polymer fibers and absorbent fibers. Coform materials and coforming processes are known in the art and by way of example are described in U.S. Pat. No. 4,100,324 to Anderson, et al.; U.S. Pat. No. 5,284,703 to Everhart, et al.; and U.S. Pat. No. 5,350,624 to Georger, et al.; each of which are hereby incorporated by reference to the extent that they are consistent (i.e., not in conflict) herewith.

In a particular aspect, the matrix of fibers 78 may be provided by a coform composite that can be a blend of meltblown polymer fibers and cellulosic fibers. Various suitable materials may be used to provide the meltblown fibers such as a polyolefin material. Alternatively, the polymer fibers may be stretch polymer fibers, such as those provided by a copolymer resin. For instance, Vistamaxx® elastic olefin copolymer resin designated PLTD-1819 available from ExxonMobil Corporation of Houston, Tex. or KRATON G-2755 available from Kraton Polymers of Houston, Tex. may be used to provide stretchable polymer fibers for the matrix of fibers 78. Other suitable polymeric materials or combinations thereof may alternatively be utilized as are known in the art.

Further, various absorbent cellulose fibers may be utilized, such as NF 405, a chemically treated bleached southern softwood Kraft pulp available from Weyerhaeuser Co. of Federal Way, Wash. U.S.A.; NB 416, a bleached southern softwood Kraft pulp available from Weyerhaeuser Co.; CR-0056, a fully debonded softwood pulp available from Bowater Inc. of Greenville S.C., Golden Isles 4822 debonded softwood pulp available from Koch Cellulose of Brunswick, Ga., U.S.A.; and SULPHATATE HJ, a chemically modified hardwood pulp available from Rayonier Inc. of Jesup, Ga. U.S.A.

The polymer fibers and the meltblown fibers may be coformed to provide the matrix of fibers 78 by providing a stream of absorbent fibers and a stream of extruded molten polymeric fibers. Further, to provide the temperature change composite 72, a stream of temperature change material 80 can also be provided. These streams can be merged into a single stream and collected on a forming surface such as a forming belt or forming drum to form the temperature change composite 72 of the temperature change member 70. Optionally, a forming layer, such as first carrier layer 74, can be placed on the forming surface and used to collect the materials included in the temperature change composite 72.

The stream of absorbent fibers may be provided by feeding a pulp sheet into a fiberizer, hammermill, or similar device as are known in the art. Suitable fiberizers are available from Hollingsworth of Greenville, S.C. and are described in U.S. Pat. No. 4,375,448 issued Mar. 1, 1983 to Appel et al. The stream of polymer fibers may be provided by meltblowing a copolymer resin or other polymer. In particular, the melt temperature for a copolymer resin such as Vistamaxx® PLTD 1810 can be from 450 degrees F. (232 degrees C.) to 540 degrees F. (282 degrees C.) to improve the entrainment of the temperature change material in the matrix. As mentioned above, suitable techniques for producing nonwoven fibrous webs, which include meltblown fibers, are described in the previously incorporated U.S. Pat. Nos. 4,100,324 and 5,350,624. The meltblowing techniques can be readily adjusted in accordance with conventional know-how to provide turbulent flows that can operatively intermix the fibers and the temperature change material 80. For example, the primary air pressure may be set at 5 psi and the meltblown nozzles may be 0.020 inch spinneret hole nozzles. The techniques can also be readily adjusted in accordance with conventional knowledge to provide the desired weight percentages of the various materials in the temperature change composite 72.

The stream of temperature change material 80 may be pneumatically provided or gravity fed. A suitable method and apparatus for delivering material in an airstream is described in U.S. Pat. No. 4,604,313 issued Aug. 5, 1986 to McFarland et al.; the disclosure of which is incorporated by reference herein to the extent that it is consistent (i.e., not in conflict) herewith. The coform material may also include other materials, such as superabsorbent materials.

In one aspect, the temperature change composite 72 provided by a coform composite as described above may be from 5 to 15 percent by weight meltblown polymer fibers, 10 to 50 percent by weight absorbent fibers and 40 to 80 percent by weight temperature change material. In a particular aspect, the temperature change composite 72 can be 8 percent by weight meltblown polymer fibers, 14 percent by weight absorbent fibers, 78 percent by weight temperature change material and define a basis weight of 1340 gsm.

In particular aspects where the temperature change composite 72 is provided by a coform composite as described above, portions of the temperature change composite can act as a distribution layer similar to the surge management layer described above. That is, upon one or more insults, the temperature change material 80 that was present in the insult area can be consumed, but the remaining coform material in the temperature change composite can act to distribute future insults both to other regions of the temperature change member 70, thereby more effectively alerting the wearer to future insults, and to other regions of the absorbent body 44 to improve the performance of the pants 20.

As mentioned above, the temperature change member 70 can optionally include a first carrier layer 74 (FIGS. 4 and 5) in superposed relationship with the temperature change composite 72. Further, the temperature change member 70 can optionally include a first carrier layer 74 and a second carrier layer 76 (FIG. 5) where the first carrier layer and the second carrier layer 76 sandwich the temperature change composite 72. The first and second carrier layers 74 and 76 may be provided by separate webs of material, or alternatively can be provided by a single web of material that is folded in half about the temperature change composite 72.

In certain aspects, the carrier layers 74 and 76 can be liquid permeable or liquid impermeable. For instance, one carrier layer, such as the first carrier layer 74 may be at least partially liquid impermeable, and optionally substantially or completely liquid impermeable and the other carrier layer, (i.e., the second carrier layer 76 can be at least partially liquid permeable and optionally substantially or completely liquid permeable. In such an aspect, the first carrier layer 74 can be disposed toward the outer surface 32 and the second carrier layer 76 can be disposed toward the inner surface 30. As such, liquid insults may pass through the second carrier layer 76 to activate the temperature change material, and the first carrier layer 74 can slow the flow of the liquid insult from leaving the temperature change member 70 thus maximizing the temperature change that can be felt by the wearer. Alternatively, the first carrier layer 74 can be liquid permeable, and in aspects with a second carrier layer 76, both carrier layers 74 and 76 may be liquid permeable. In yet another alternative, the carrier layers 74 and 76 can each include portions that are liquid permeable and liquid impermeable. Carrier layers 74 and 76 as described above can further improve the integrity of the temperature change member 70 thereby enhancing processability, and can also aid in retaining the temperature change material within the member 70.

Suitable liquid permeable materials for the carrier layers 74 and 76 include tissue layers, nonwoven layers, or combinations thereof. In particular, materials described as suitable for use as the bodyside liner 42 may also be suitable for a liquid permeable carrier layer 74 and 76. Accordingly, a liquid permeable carrier layer 74 and 76 can also be stretchable. Likewise, materials described as suitable for use as the outercover 40 may be suitable for use as a liquid impermeable carrier layer 74 and 76. Accordingly, a liquid impermeable carrier layer 74 and 76 can also be stretchable.

The temperature change material 80 of the various aspects of the present invention can include a substance that provides a temperature change when placed near the wearer and contacted with urine. The temperature change can be either an absorption or release of heat that is noticeable to the wearer. Absorption of heat by the temperature change material 80 will provide the wearer with a cool sensation, while a release of heat by the substance will provide the wearer with a warm sensation. Reference is made to U.S. Patent Application Publication 2004/0254549, published Dec. 16, 2004, in the name of Olson, et al., incorporated by reference herein, for additional information regarding the mechanism by which the temperature change sensation is accomplished. Suitably, the temperature change material 80 can be provided in particulate form for ease of processing in the described aspects.

The temperature change material 80 can be homogeneously intermixed within the thickness of said matrix of fibers 78. Alternatively, the temperature change material 80 can define a distribution gradient within the thickness of the temperature change composite 72. For example, the temperature change material 80 may be intermixed within the matrix of fibers 78 in greater amounts toward the inner surface 30 of the pants. Alternatively, the temperature change material 80 may be intermixed within the matrix of fibers 78 in greater amounts toward the outer surface 30 of the pants.

The temperature change material 80 is responsive to contact with an aqueous solution such as urine to either absorb or release heat. The mechanism by which this is accomplished is dissolution of the substance in the aqueous solution, swelling of the substance in the aqueous solution, or reaction of the substance in the aqueous solution. For example, the temperature change material may include particles that have a substantial energy difference between a dissolved state and a crystalline state so that energy in the form of heat is absorbed or released to the environment upon contact with urine, or the temperature change material may release or absorb energy during swelling or reacting in an aqueous solution.

While a wide variety of substances may result in a temperature change when contacted with an aqueous solution, the selection of a particular temperature change material 80, the determination of the amount to be used and the location of the substance should be based in part on the desired temperature change. Specifically, the temperature change member 70 may suitably provide the training pants 10 with a temperature change (i.e., cooler or warmer) when wet of at least about 5 degrees C., more suitably about 10 degrees C., still more suitably about 15 degrees C. Alternatively, the temperature change member 70 can provide the pant 20 with a surface temperature change when wet of from 5 degrees C. to 15 degrees C. Surface temperature changes within this range are believed to be identifiable to some extent by children of toilet training age. More suitably the temperature change member 70 can provide the pant 20 with a surface temperature change when wet of from 5 degrees C. to 10 degrees C.

Thus, in a particular aspect, where the temperature change material is endothermic, a drop in the temperature of the product when insulted can be from about 37 degrees C. to about 25 degrees C., and further to about 22 degrees C. for improved effectiveness, particularly with a preoccupied wearer (i.e., a playing child). The temperature change can suitably last for at least 10 minutes, and more suitably for approximately 15 minutes.

By way of example, polyols such as Xylitol particles may be selected to provide a cooling sensation as Xylitol particles absorb heat when dissolved in an aqueous solution. Alternatively, other polyols such as Sorbitol or Erithritol may be advantageously selected to provide a cooling sensation. In yet another alternative, various combinations of the above temperature change materials may be utilized.

Other suitable temperature change materials that absorb heat during dissolution include salt hydrates, such as sodium acetate ($H_2O$), sodium carbonate ($10H_2O$), sodium sulfate ($10H_2O$), sodium thiosulfate ($5H_2O$), and sodium phosphate ($10H_2O$); anhydrous salts such as ammonium nitrate, potassium nitrate, ammonium chloride, potassium chloride, and sodium nitrate; organic compounds such as urea and the like or combinations thereof.

The temperature change material 80 may also include those substances that absorb or release heat during swelling. By way of illustration, one suitable temperature change material that releases heat during swelling is a lightly cross-linked partially neutralized polyacrylic acid. Other temperature change material 80 that releases heat during dissolution includes aluminum chloride, aluminum sulfate, potassium aluminum sulfate, and the like or combinations thereof.

The temperature change material 80 can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued to Greenberg, and U.S. Pat. No. 5,266,592 issued to Grub et al.

Thus, as described above, the temperature change member 70 can include a matrix of fibers 72 and the temperature change material 80, such as Xylitol particles, intermixed within the matrix of fibers 72. Once wet by urination, the Xylitol dissolves, creating an endothermic response, thereby signaling to the wearer that urination has occurred.

The temperature change member 70 is disposed within the training pants 20 so that, upon urination, liquid makes contact with the temperature change material 80. For example, the temperature change member 70 can be disposed with the absorbent body 44, for example intermediate the outercover 40 and liner 42. In particular, the temperature change member 70 may be attached to the absorbent body 44 and disposed toward the inner surface of the pants 20. Alternatively, the temperature change member 70 may be attached to the liner 42 adjacent the absorbent body 44. In still yet another alternative, the temperature change member 70 can be disposed within a gap between potions of the absorbent body 44 and attached, for example, to the outercover 40. Such an aspect is described in U.S. patent application Ser. No. 10/955,534 filed Sep. 29, 2004, in the name of Weber, et al., the disclosure of which is incorporated by reference to the extent that it is consistent (i.e., not in conflict) herewith.

As can be readily appreciated, the temperature change member 70 can be of various shapes and sizes. For example, the temperature change member 70 can be rectangular and can have a width in the lateral direction 48 of from 2.5 cm to 10 cm and a length in the longitudinal direction 46 of from 2.5 cm to 25 cm. In one aspect the temperature change member 70 can measure about 8 cm by about 10 cm. Alternatively, the temperature change member 70 can be oval in shape, circular, triangular, or the like. In yet another alternative, the temperature change member 70 can be generally be provided in strips that extend in the lateral 48 or longitudinal direction 46 and that can be separated by a gap. Further, it will be understood by those of skill in the art that the training pants 20 of the present invention could include more than one temperature change member 70.

Therefore, as can be readily appreciated, the pants 20 of the various aspects of the present invention provide a temperature change member 70 that can more readily and effectively signal urination to the wearer, even when deformed or buckled in the crotch of the wearer in use.

A suitable procedure for determining the temperature change when wet of a product containing a temperature change material is described below in the temperature change test as follows. The test should be conducted in an environment having a stable temperature of 21 degrees C. to 22 degrees C. and a stable humidity of about 50 percent. The product to be tested is prepared by removing any elastic side panels and cutting all other elastics to permit the product to lay as flat as possible. The product is positioned in a Plexiglas cradle to simulate the configuration of the product in actual use. The center of the product is placed in the deepest portion of the cradle.

A liquid dispensing nozzle operatively connected to a liquid dispensing pump is positioned to dispense saline onto the inner surface of the product. The tip of the nozzle should be located 1 cm away from the inner surface and 10 cm forward of the center of the product, along the product's longitudinal axis. The pump is activated to dispense 90 ml of a stabilized isotonic 0.9 percent saline at a rate of 15 ml/sec. The saline is certified blood bank saline available from The Baxter Healthcare Corporation, Scientific Products Division, McGraw Park, Ill., and is at a temperature of 37° C.

The surface temperature of the product at the location of the temperature change member is measured using a standard thermometer or temperature sensing thermistors connected to a digital display or recording device. The surface temperature 30 seconds after the saline is dispensed is recorded as the test temperature. A reference temperature is obtained by performing this test on a portion of the product not including the temperature change material or on a similar product without the temperature change material. The surface temperature change when wet for the product is the difference between the test temperature and the reference temperature.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article defining a longitudinal direction, a lateral direction perpendicular to the longitudinal direction, an article first side edge and an article second side edge opposite said article first side edge and a pair of end edges, said absorbent article comprising:
 a liquid impermeable outercover;
 an absorbent body disposed on said outercover; and
 a temperature change member disposed with said absorbent body, said temperature change member comprising temperature change material disposed with said temperature change member, wherein the temperature change member defines a first temperature change member region and a second temperature change member region disposed in a lateral direction from the first temperature change member region, each temperature change member region including a nonzero amount of temperature change material, wherein the first temperature change member region comprises a greater amount of temperature change material by weight than the second temperature change member region, and wherein said temperature change member provides said article with a temperature change of at least 5 degrees C., as determined by the temperature change test described herein.

2. The absorbent article of claim 1 wherein said temperature change member further comprises a coform matrix of fibers, said coform matrix of fibers comprising polymer fibers and absorbent fibers, and wherein said temperature change material is intermixed within said coform matrix of fibers.

3. The absorbent article of claim 1 wherein said temperature change material is an endothermic material.

4. The absorbent article of claim 1 wherein said temperature change material is an exothermic material.

5. The absorbent article of claim 1 wherein said temperature change material comprises xylitol.

6. The absorbent article of claim 1 wherein said temperature change material comprises sorbitol.

7. The absorbent article of claim 1 wherein said temperature change material comprises erithritol.

8. The absorbent article of claim 1, wherein the temperature change member provides the article with a surface temperature change when wet of at least 10 degrees C., as determined by the temperature change test described herein.

9. The absorbent article of claim 1, wherein the temperature change member provides said article with a surface temperature change when wet of from 5 to 15 degrees C., as determined by the temperature change test described herein.

10. An absorbent article defining a longitudinal direction, a lateral direction perpendicular to the longitudinal direction, an article first side edge and an article second side edge opposite said article first side edge and a pair of end edges, said absorbent article comprising:
 a liquid impermeable outercover;
 an absorbent body disposed on said outercover; and
 a temperature change member disposed with said absorbent body, said temperature change member comprising temperature change material disposed with said temperature change member in a nonuniform distribution by weight across said temperature change member in said lateral direction, wherein said temperature change member provides said article with a temperature change of at least 5 degrees C., as determined by the temperature change test described herein, and wherein said temperature change member defines a first temperature change member region, a second temperature change member region, and a third temperature change member region between said first temperature change member region and said second temperature change member region, wherein said first temperature change member region and said second temperature change member region comprise a greater amount of temperature change material by weight than said third temperature change member region.

11. The absorbent article of claim 10 wherein said first temperature change member region and said second temperature change member region comprise substantially the same amount of said temperature change material by weight.

12. The absorbent article of claim 10 wherein said temperature change member defines a temperature change member first side edge and a temperature change member second side edge opposite said temperature change member first side edge wherein said first temperature change member region is proximate said temperature change member first side edge and said second temperature change member region is proximate said temperature change member second side edge.

13. The absorbent article of claim 12 wherein said first temperature change member region and said second temperature change member region each define a higher density than said third temperature change member region.

14. The absorbent article of claim 12 wherein said first temperature change member region and said second temperature change member region each define a density of at least 0.20 grams/cm$^3$.

15. The absorbent article of claim 12 wherein said first temperature change member region and said second temperature change member region each define a density of between 0.25 grams/cm$^3$ and 0.45 grams/cm$^3$.

16. The absorbent article of claim 10 wherein said temperature change member defines a total amount of temperature change material and said third temperature change member region comprises at least 10% by weight of said total amount of temperature change material.

17. The absorbent article of claim 10 wherein said temperature change member defines a total amount of temperature change material and said third temperature change member region comprises less than 5% by weight of said total amount of temperature change material.

18. The absorbent article of claim 10 wherein said first temperature change member region and said second temperature change member region each comprise at least 10% more of said temperature change material by weight than said third temperature change member region.

19. The absorbent article of claim 10 wherein said temperature change member defines a total amount of temperature change material and wherein said first temperature change member region and said second temperature change member region together comprise at least 60% of said total amount of temperature change material by weight.

20. An absorbent article defining a longitudinal direction, a lateral direction perpendicular to the longitudinal direction, an article first side edge and an article second side edge opposite said article first side edge and a pair of end edges, said absorbent article comprising:
 A liquid impermeable outercover;
 An absorbent body disposed on said outercover; and
 A temperature change member disposed with said absorbent body, said temperature change member defining a temperature change member first side edge, a temperature change member second side edge opposite said temperature change member first side edge, a first temperature change member region, a second temperature change member region, and a third temperature change member region between said first temperature change member region and said second temperature change member region, said temperature change member comprising temperature change material disposed with said temperature change member in a nonuniform distribution by weight across said temperature change member in said lateral direction, wherein said first temperature change member region and said second temperature change member region comprise a greater amount of temperature change material by weight than said third temperature change member region, and wherein said temperature change member provides said article with a temperature change of at least 5 degrees C., as determined by the temperature change test described herein.

21. The absorbent article of claim 20 wherein said first temperature change member region and said second temperature change member region each define a higher density than said third temperature change member region.

22. The absorbent article of claim 20 wherein said temperature change material is an endothermic material.

23. The absorbent article of claim 20 wherein said temperature change member further comprises a coform matrix of fibers, said coform matrix of fibers comprising polymer fibers and absorbent fibers, and wherein said temperature change material is intermixed within said coform matrix of fibers.

24. The absorbent article of claim 20, wherein the temperature change member provides said article with a surface temperature change when wet of from 5 to 15 degrees C., as determined by the temperature change test described herein.

* * * * *